(12) United States Patent
Ferguson

(10) Patent No.: US 6,884,341 B2
(45) Date of Patent: Apr. 26, 2005

(54) FILTER DEVICE TO CAPTURE A DESIRED AMOUNT OF MATERIAL

(75) Inventor: Gary W. Ferguson, Burnaby (CA)

(73) Assignee: G6 Science Corp. (CA)

( * ) Notice: Subject to any disclaimer, the term of this patent is extended or adjusted under 35 U.S.C. 154(b) by 38 days.

(21) Appl. No.: 10/263,129

(22) Filed: Oct. 2, 2002

(65) Prior Publication Data

US 2004/0065622 A1 Apr. 8, 2004

(51) Int. Cl.$^7$ ............................................. B01D 29/60
(52) U.S. Cl. .................... 210/132; 210/446; 73/862.23; 73/61.73; 436/177; 422/101; 137/550
(58) Field of Search ................................ 210/431, 430, 210/432, 132, 97, 120, 137, 91, 359, 390, 398, 477, 418, 349, 395, 446, 131; 137/547, 484.4, 484.6, 504, 550; 73/823.24, 61.73, 863.23, 863.01, 863.02, 863.03; 436/177; 422/101, 103

(56) References Cited

U.S. PATENT DOCUMENTS

| | | | |
|---|---|---|---|
| 2,151,538 A | * | 3/1939 | Swanson ..................... 210/131 |
| 3,388,800 A | * | 6/1968 | Macgregor .................. 210/131 |
| 3,591,003 A | | 7/1971 | Cooper |
| 3,662,887 A | * | 5/1972 | Uhlhorn, Jr. ................. 210/131 |
| 3,886,968 A | * | 6/1975 | Murrell ....................... 137/501 |
| 3,963,048 A | | 6/1976 | Bowman |
| 4,246,788 A | | 1/1981 | Olin et al. |
| 4,250,830 A | | 2/1981 | Leif |
| 4,284,505 A | | 8/1981 | Pope |
| 4,319,996 A | | 3/1982 | Vincent |
| 4,395,493 A | | 7/1983 | Zahniser |
| 4,435,507 A | | 3/1984 | Stenkvist |
| 4,614,109 A | | 9/1986 | Hofmann |
| 4,765,963 A | | 8/1988 | Mukogawa et al. |
| 4,792,398 A | | 12/1988 | Klein |
| 4,832,840 A | | 5/1989 | Klinkau |
| 4,961,432 A | | 10/1990 | Guirguis |
| 4,967,791 A | | 11/1990 | Sternberger |
| 4,969,997 A | | 11/1990 | Kluver |
| 4,996,627 A | | 2/1991 | Zias |
| 5,141,639 A | | 8/1992 | Kraus |
| 5,168,965 A | | 12/1992 | Huang |
| D343,682 S | | 1/1994 | Cattaoris |
| 5,312,380 A | | 5/1994 | Alchas |
| 5,341,838 A | | 8/1994 | Powell |
| 5,358,690 A | | 10/1994 | Guirguis |
| 5,422,273 A | | 6/1995 | Garrison |
| 5,429,803 A | | 7/1995 | Guirguis |
| 5,469,883 A | * | 11/1995 | Lee .......................... 137/513.3 |
| 5,471,994 A | | 12/1995 | Guirguis |
| 5,480,484 A | | 1/1996 | Kelley |
| 5,500,167 A | | 3/1996 | Degen |
| 5,561,556 A | | 10/1996 | Weissman |

(Continued)

FOREIGN PATENT DOCUMENTS

| | | | |
|---|---|---|---|
| CH | 615029 A5 | * 12/1979 | ............ G05D/7/01 |
| WO | WO 01/83089 | 11/2001 | |

Primary Examiner—Terry K. Cecil
(74) Attorney, Agent, or Firm—Trexler, Bushnell, Giangiorgi, Blackstone & Marr, Ltd.

(57) ABSTRACT

A filter device is used to capture a desired amount of material suspended in a liquid or gas. The device includes a planar filter 530 mounted in a chamber defined by a body member having an upper body 510, a lower body 520, an inlet port 525, and an outlet port 515. The filter includes porous portions 540 and 545. Porous portion 545 is centrally arranged and is more restrictive to flow than portion 540. The filter is designed such that upon portion 540 capturing a desired amount of material, a predetermined pressure change exists across the filter. The predetermined pressure change causes the filter to deform and conform against an inner surface of the upper body resulting in all suspension flowing through the apparatus to flow through the more restrictive second portion 545.

1 Claim, 8 Drawing Sheets

U.S. PATENT DOCUMENTS

| | | |
|---|---|---|
| 5,593,529 A | 1/1997 | Grimes |
| 5,603,827 A | 2/1997 | Hermann |
| 5,679,154 A | 10/1997 | Kelley |
| 5,744,034 A | 4/1998 | Clapham et al. |
| 5,784,193 A | 7/1998 | Ferguson |
| 5,792,425 A | 8/1998 | Clark |
| 5,849,505 A | 12/1998 | Guirguis |
| 5,976,824 A | 11/1999 | Gordon |
| 6,010,909 A | 1/2000 | Lapidus |
| 6,091,483 A | 7/2000 | Guirguis |
| 6,106,483 A | 8/2000 | Guirguis |
| 6,149,871 A | 11/2000 | Guirguis |
| 6,162,401 A | 12/2000 | Callaghan |
| 6,210,909 B1 | 4/2001 | Guirguis |
| 6,215,892 B1 | 4/2001 | Douglass |
| 6,225,125 B1 | 5/2001 | Lapidus |
| 6,286,372 B1 | 9/2001 | Von Rauch |
| 6,295,877 B1 | 10/2001 | Aboul-Hosn |
| 6,296,764 B1 | 10/2001 | Guirguis |
| 6,309,362 B1 | 10/2001 | Guirguis |
| 6,318,190 B1 | 11/2001 | Radcliffe et al. |
| 6,404,906 B2 | 6/2002 | Bacus |
| 6,425,883 B1 | 7/2002 | Urich |
| 6,579,447 B2 | 6/2003 | Romanyszyn et al. |

\* cited by examiner

FILTER DEVICE TO CAPTURE A DESIRED AMOUNT OF MATERIAL

BACKGROUND OF INVENTION

In industry and biology it is often advantageous to capture particulate material suspended in a liquid or gas, on a filter for purification, enrichment, observation or subsequent analysis. The quantity and characteristics of particulate material is important in manufacturing, for example, processes that utilize powders, pigments, fuels or lubricants. Particle evaluations are also used to assess contaminants in water or air such as pollen, asbestos and soot. Particulate material is sometimes used indirectly to assess proteins or chemicals, for example, beads coated with monoclonal antibody may be interacted with blood. Then these beads may be captured on a filter and assessed for bound protein.

As used herein, "sample suspension" means particulate material suspended in a liquid or gas. "Material" as used herein means biological cells, organisms, bacteria, viruses, or components of these, as well as organic and inorganic particulates or any other matter which may be captured or isolated on a filter. This captured material may be subsequently used to provide diagnostic and/or analytical information or be re-suspended or otherwise used. For example, captured material may be analyzed chemically or may be placed on a receiving surface, such as a microscope slide for analysis.

Although there are a number of established methods to deposit mono-layers of material on a receiving surface for observation or analysis, controlling the amount of material collected on a filter is more difficult to achieve. Typically, electronic control and intervention is required to monitor and control the collection of material on a filter apparatus and/or other laboratory methods (employing particle counters and dilution techniques) are used to adjust the concentration of the material in suspension. Unfortunately, these methods require additional apparatus and electronics, and are relatively complex or expensive in terms of supplies, and time. Therefore, a simple, reliable method of capturing a desired amount of material on a filter would be advantageous.

The present invention is a filter device that provides a means to collect a desired amount of material. To accomplish this, a pressure sensor is used substantially to monitor the flow rate through the filter. In addition, the pressure sensor may be combined with a valve that provides control over sample flow, and thus the collection of material. In one embodiment of the present invention, a pressure sensor and valve are integrated to form a pressure-sensitive check valve. In other embodiments the membrane filter or filter assembly themselves deform, acting as a pressure sensor and flow control mechanism.

BRIEF DISCUSSION OF PRIOR ART

U.S. Pat. No. 3,591,003, to Cooper, entitled "Differential pressure-responsive signaling device and filter assembly having same" discusses removal of contaminants from fluids such as lubricating oil, coolants and fuel. As the filter becomes obstructed with contaminants, the pressure differential across the filter increases (as sensed by the occurrence of a predetermined pressure differential) indicating that the filter is clogged and should be serviced.

The principles of monitoring and responding to flow conditions are exploited for various embodiments of the present invention.

U.S. Pat. No. 3,963,048, to Bowman, entitled "Poppet valve assembly" discusses a miniature poppet valve for controlling the flow of a pressurized gas, which is small, reliable, sturdy and resistive to damage.

U.S. Pat. No. 4,792,398, to Klein, entitled, "Manual vacuum filtration device" discusses a porous membrane filter element interposed between a specimen receiving chamber and a vacuum chamber to retain solid particulate on the filter element. Further this prior art discusses recent attempts to provide apparatus for liquid filtering which are relatively small and operate by manual manipulation to cause a pressure differential. Limitations cited include close tolerances and associated costs. The apparatus discussed provides for a unidirectional valve to release air from the vacuum chamber. In one embodiment, a unidirectional valve mechanism includes a plurality of air passages or orifices formed equidistantly circumferentially spaced in relation about the annular stepped wall of the device to provide a desired rate of air discharge (a means of vacuum regulation). Various filters and apparatus that could be suitable exploited for the present invention are also discussed. A means to release vacuum or otherwise substantially reduce sample flow is utilized within various embodiments of the present invention.

U.S. Pat. No. 5,168,965 to Huang, entitled, "Bypass valve with selective characteristics for controlled and adjustable dashpots" discusses pressure activated check valves and means to dictate characteristics for use in motor vehicles, for example. These principles are utilized within various embodiments of the present invention.

U.S. Pat. No. 6,296,764 to Guirguis, entitled "Apparatus for mixing and separating particulate matter from a fluid" discusses a rotatable agitator and issues related to efficiently collecting and concentrating particulate matter in a form readily accessible for microscopic examination. Also noted: "Conventional cell preparation techniques fail to adequately address the issues of non-uniform cell densities, uneven cell distribution and air drying artifacts."

U.S. Pat. Nos. 5,471,994, 6,091,483 and 6,106,483, also to Guirguis, describe various methods of capturing material on filter apparatus. And in U.S. Pat. No. 4,961,432, entitled, "Modular fluid sample preparation assembly" Guirguis describes what is essentially a syringe (cylindrical hollow piston with exterior mounted fluid tight seal) to move a fluid sample, and more particularly the capture of particulate matter on filters. While this prior art generally seeks to provide means to deposit a uniform density cell monolayer, it acknowledges problems and limitations, such as material overlap, which are related to the amount of material captured. Providing improved control over the amount of material captured on a filter is an object of the present invention.

U.S. Pat. No. 4,319,996, to Vincent, entitled, "Filter with initially flat membrane and curved membrane support", describes a filter device with interposed deformable membrane filter that takes on the shape of the support surface during use. The present invention in various embodiments utilizes a deformable filter or support structure to derive novel functionality in the form of pressure monitoring and/or flow control.

An alternative method of providing a desired quantity of material is discussed in co-pending U.S. patent application by Ferguson et al., filed Aug. 26, 2002, application Ser. No. 10/228,353, entitled, "Methods of depositing density gradients of material from sample suspensions and filter device for same". These innovations provide a means to capture a concentration gradient of material, allowing the user to select a region with a desired amount of material for microscopic examination, for example.

Various centrifuge systems also seek concentrate material and/or provide material for monolayer deposition, for example, U.S. Pat. No. 4,250,830 to Leif entitled "Swinging Buckets", U.S. Pat. No. 5,480,484 to Kelly entitled "Cytology centrifuge apparatus" and U.S. Pat. No. 5,679,154 to Kelly entitled "Cytology centrifuge apparatus", and U.S. Pat. No. 6,162,401 to Callaghan entitled, "Cytofunnel arrangement".

U.S. Pat. No. 4,395,493 to Zahniser entitled "Monolayer device using filter techniques", discusses the need to have proper cell concentration in liquid suspension and a means to obtain a quantity of liquid having a desired number of cells as measured for example, with an impedance cell counter. This patent also describes use of filter tape as a receiving surface.

U.S. Pat. No. 4,614,109 to Hofmann entitled "Method and device for testing the permeability of membrane filters" provides for testing membrane permeability, and in combination with U.S. Pat. No. 3,591,003, to Cooper, and U.S. Pat. No. 4,792,398, to Klein (discussed above) provide a basis for U.S. Pat. No. 6,010,909, to Lapidus, entitled "Method and apparatus for controlled instrumentation of particles with a filter device", and U.S. Pat. No. 6,225,125, to Lapidus, also entitled, "Method and apparatus for controlled instrumentation of particles with a filter device". Hofmann discusses means to assess the concentration, and size of membrane pores as indicated by the differential pressure across the membrane as pores clear. Lapidus measures the differential pressure across a membrane as pores are blocked. The preferable membrane filter "is aperaturized with a uniform distribution of pores of substantially uniform size to block cells and other particles above a threshold size determined by the size of pores and to freely pass smaller particles". The latter provides an indication of cell concentration, rather than membrane characteristics. Similarly, it is an object of the present invention to provide such functionality by relatively simple and inexpensive means.

U.S. Pat. No. 6,295,877 to Aboul-Hosn, entitled "Pressure sensing cannula" discusses pressure transducers mounted in a hollow body, such as a the tubular wall defining the main lumen of a cannula for the purpose of determining flow rate or body fluids, such as blood, for example.

U.S. Pat. No. 4,967,791 to Stemberger, entitled "Pressure activated check valve" discusses moving a poppet valve assembly to a closed position in opposition to a spring and elements responsive to fluid pressure in an inlet port. The present invention contemplates various embodiments utilizing a pressure-sensitive check valve to determine flow rate and provide control over sample flow by either closing the flow path or removing the pressure causing sample flow.

U.S. Pat. No. 5,341,838, to Powell, entitled "Direct spring pressure operated valve" discusses the use of a valve as a safety relief valve, for example. Pressure above the valve member causes the valve member to trigger and drop inlet pressure to a predetermined level. Various mechanical means may be used to adjust a pressure sensor, such as springs, tabs, levers, etc. Similarly, various means such as potentiometers permit electromechanical pressure sensors to be adjusted to trigger at a predetermined pressure. Alternatively, pressure transducers and/or valves may have trigger characteristics which are fixed during design. The present invention discusses various embodiments which rely on triggering, deforming or otherwise reacting to a predetermined pressure, and more particularly where differential pressure across a membrane is used to subsequently adjust sample flow rate, for example, to half flow when a predetermined amount of material has been collected on a filter.

U.S. Pat. No. 6,425,883, to Urich, entitled "Method and apparatus for controlling vacuum as a function of ultrasonic power in an ophthalmic phaco aspirator" among other things, discusses a control valve to allow a fluid into an aspiration line. The system may include a pressure transducer coupled to the aspiration line and a check valve.

As has been discussed various means exist to monitor and control flow rate using pressure transducers and valves. Additional details regarding transducers, their characteristics and methods of fabrication may also be found in U.S. Pat. No. 4,996,627 to Zias, entitled, "High sensitivity miniature pressure transducer".

It is therefore an object of the present invention to provide a filter device to capture a desired amount of material in a simple, cost effective manner. It is a further object of the present invention to provide a method that can be used to prepare multiple samples, simultaneously. It is a further object of the present invention, to provide a method that can be further automated.

Methods to predetermine and set the trigger point for pressure transducers for various applications, guides to selecting filters and materials for various applications and other general principals are discussed in the prior art, therefore, the prior art cited in this application is included by reference herein.

SUMMARY

It would be beneficial to provide a simple filter apparatus to capture a desired amount of material on a filter that does not rely on relatively complex electronics and sensors. In addition, it would be advantageous to provide a filter capture method that can be automated to prepare a plurality of samples, simultaneously. Accordingly, as will be further described, the present invention provides a novel apparatus incorporating a pressure transducer and means to substantially halt or otherwise adjust sample flow, providing a simple, reliable device to capture a desired amount of material without complex electronics. In addition, the present invention is easily automated to allow material from a plurality of samples to be captured on a membrane filter, simultaneously.

As previously discussed herein, a variety of pressure sensors are available with appropriate characteristics for exploitation within the present invention. For some applications material captured on a filter is intended for contract-transfer to a receiving surface, such as a microscope slide. Accordingly, for some applications when a relatively large filter is required, or the suspending fluids are viscous, for example, a filter support structure may be desirable.

The present invention provides a filter apparatus using means to measure or sense the flow rate of a gas or liquid through a filter. In some embodiments pressure is sensed, however, the flow rate of a fluid or gas could also be sensed. In some embodiments, the present invention terminates or otherwise adjusts sample flow when a predetermined amount of material has been captured on a filter for example by venting the pressure differential responsible for sample flow, or closing the flow pathway, for example with a valve. In other embodiments of the present invention material collection on a filter is substantially reduced by restricting access to the filter, for example, by changing its position or deforming its shape.

Filter types include fibrous and mesh membranes, porous and capillary porous membranes, and fabric and gel lattices, for example. Such filters are commonly made from paper, nylon, glass fibers, nitrocellulose, polypropylene, chemical gels etc. In some cases filters are further treated to enhance certain properties such as capture capacity, flexibility, selectivity or adherence by coating them or incorporating other compounds such as PTFE or protein binding compounds. Accordingly, filters can be formed in various shapes such as planar, conical, pyramidal, hemispherical, spherical or filters may have their shape imposed by a carrier or other support structure.

BRIEF DESCRIPTION OF THE DRAWINGS

The organization and manner of the structure and operation of the preferred embodiments of the invention, together with further objects and advantages thereof, may best be understood by reference to the following description, taken in connection with the accompanying drawings, wherein like reference numerals identify like elements in which:

FIG. 5b shows a desired amount of material collected on the syringe filter associated with FIG. 5a.

FIG. 6b further describes the filter assembly associated with FIG. 6a.

DETAILED DESCRIPTION OF THE DRAWINGS AND PREFERRED EMBODIMENTS

Figure 1A:
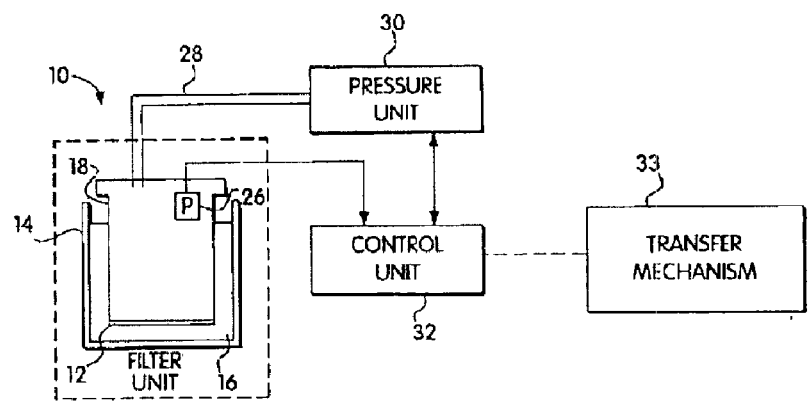
FIG. 1a (Prior art) Method to collect and monitor the concentration of material captured on a membrane filter.

While the invention may be susceptible to embodiment in different forms, there is shown in the drawings, and herein will be described in detail, specific embodiments with the understanding that the present disclosure is to be considered an exemplification of the principles of the invention, and is not intended to limit the invention to that as illustrated and described herein.

FIG. 1a (Prior art) illustrates a system 10 to collect a desired quantity of cells onto the underside of a screen-type filter 12. As diagrammed, a pressure sensor 26 is in communication with both sides of a membrane filter 12. Accordingly, one side of the membrane 12 in the collection vessel 18 is shown at ambient pressure with pressure sensor 26 provided on the opposite side of the membrane. Pressure unit 30 typically responds to electrical control signals from a control unit, which can be microprocessor-controlled, to apply selected fluid conditions to the interior of the collection vessel.

Figure 1B:
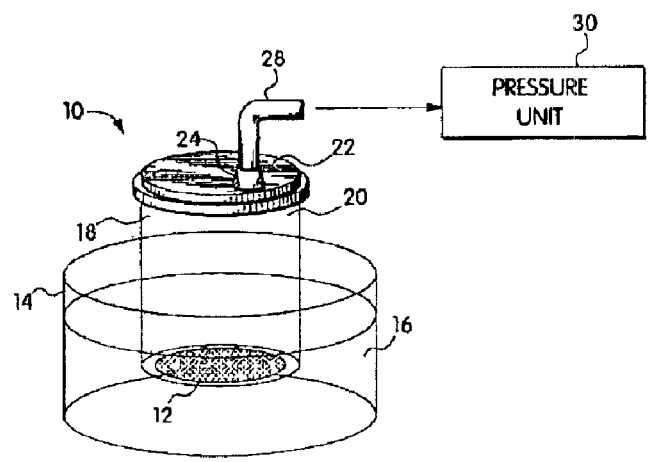
FIG. 1b (Prior art) Membrane filter device used in conjunction with FIG. 1.

FIG. 1b (Prior art) further illustrates the collection vessel 18 with screen-type filter 12 as used in this apparatus, and as described in U.S. Pat. No. 6,010,909 and again in U.S. Pat. No. 6,225,125. In this manner, a desired quantity of material may be captured.

Figure 2A:
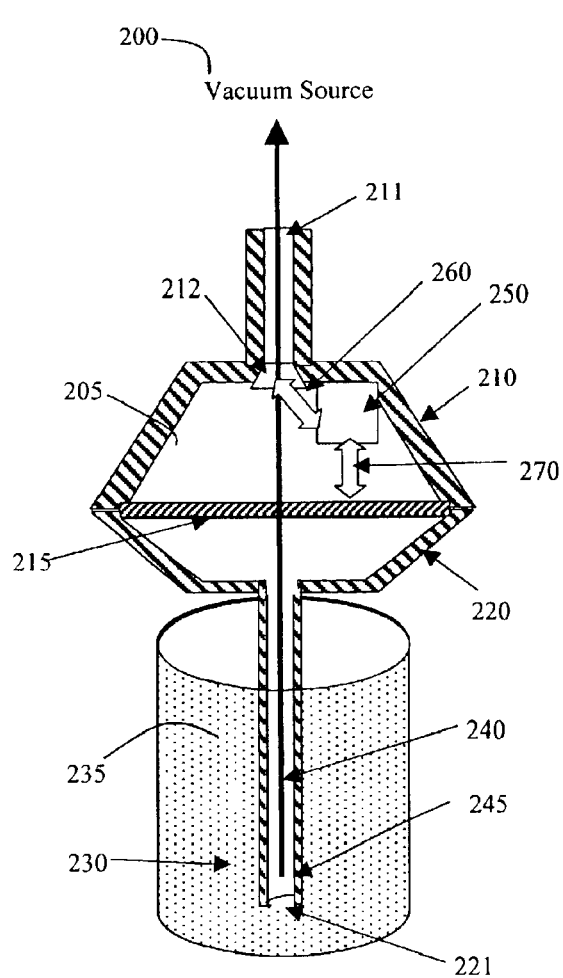
FIG. 2a shows an embodiment of the present invention capturing a desired amount of material.

FIG. 2a shows an embodiment of the present invention with filter apparatus 205 comprised of filter 215 deposed between a top body member 210 and a bottom body member 220. In this instance, open container 235 contains sample suspension 230 (e.g. particulate material suspended in a liquid) which is introduced via pickup tube 245. This pickup tube, as required or desired, may comprise part of the bottom body member 220 or pickup tube 245 may be a separate member attached to body member 220. The object of the device, which will now be further described, is to provide a means to monitor or otherwise sense the flow rate of this sample suspension 230 and to provide a means to alter, adjust, halt or otherwise influence that flow rate when indicated by a sensor 250, which is in communication (mechanically or electromechanically) with the means to control flow. Sample suspension 230 is drawn by application of pressure from vacuum source 200 therefore providing a means to cause sample suspension 230 to flow as further indicated by flow directional arrow 240, which as diagrammed, is in the inlet port 221 of the pickup tube 245, into the bottom body member 220, through the filter 215, which is this instance is a membrane filter, through a flow control element 212 (in this instance a valve) and then out through the outlet port 211. (In this embodiment, as well as in subsequently described and illustrated embodiments, vacuum is used to cause the sample suspension to flow. Other means can be used for this purpose in this and subsequent embodiments, such as gravity or mechanical means such as a pump.) Accordingly, as sample suspension 230 flows in this manner, particulate material in the sample suspension 230 begins to be captured by membrane filter 215. Pressure sensor or pressure transducer 250, in this instance contained substantially within the top body member 210, communicates with the upper surface of membrane filter 215. This communication is further indicated by communication arrow 270. Pressure sensor 250 is also in communication with flow control element 212 so as to provide a means to adjust or otherwise control flow when certain pressures are sensed. This communication between pressure sensor 250 and flow control element 212 is further indicated by communication arrow 260. Accordingly, a pressure differential is established across the membrane filter 215, thereby providing a means for the pressure sensor 250 to monitor the flow rate of the sample suspension. As sample continues to flow, and as described in association with the description of prior art in FIGS. 1 and 2, particulate material that is smaller than the pore size of the membrane filter 215 passes through the membrane (to waste or to another vessel—not shown) while material larger than the pore size of the membrane filter 215 is captured. Since filter pores provide the actual pathway through a filter, material captured by the membrane filter 215 typically blocks pores which in turn restricts flow. When the flow rate drops to a certain level, pressure sensor 250 responds (at a predetermined pressure based on the application, filter characteristic, amount of desired material etc. as previously described herein and in the prior art cited), pressure sensor 250 activates and in turn activates flow control element 212. The flow control element 212 may halt the flow of sample suspension 230 and hence stop further capture of material on the membrane filter 215, which has now captured the desired amount of material. While such a valve (flow control element 212) could be implemented in various positions of within the filter assembly 205, generally communication with pressure sensor 250 is simpler and provides more options when these two functions are relatively closely related. Further examples of this will be provided in the descriptions accompanying FIGS. 2*b* and 2*c*. Activation of the flow control element 212 may be mechanical, electromechanical or may be accomplished via further integration of the pressure sensor and valve (as will be further discussed). Similarly, these elements may be physically separate or may be functionally integrated. For applications, such as monolayer deposition, that may require access to the filter for touch or other material transfer method, the top body member 210 and bottom body member of filter apparatus 205 are preferably made separable, by employing threads or a press-fit assembly, for example.

Figure 2B:
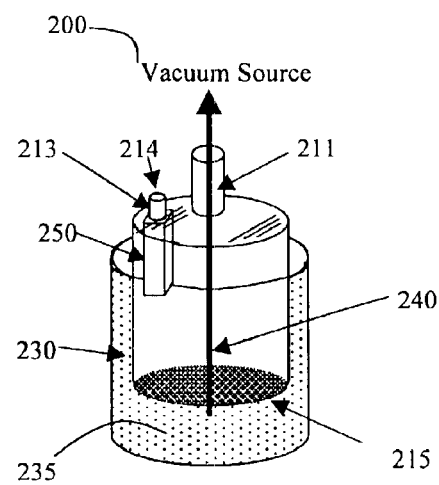
FIG. 2b shows another embodiment of the present invention capturing a desired amount of particulate material from a fluid suspension.

FIG. 2*b* shows another embodiment of the present invention with sample suspension 230 being drawn through filter 215 by application of vacuum 200. In this instance filter 215 is sealed to the bottom of upper body member 210, thereby providing access to material captured by membrane filter 215. As diagrammed the sensor 250 is integrated with flow control element 213, which in this instance provides flow control using a valve to vent the pressure source 200 through vent port 214 or flow control valve 213, rather than adjusting the sample flow pathway, as described in association with FIG. 2*a*. As required, or desired, the vent may substantially release the vacuum supplied by source 200 to halt flow, or the drop in vacuum provided by this venting may be sensed and the vacuum source, shut off.

Figure 2C:
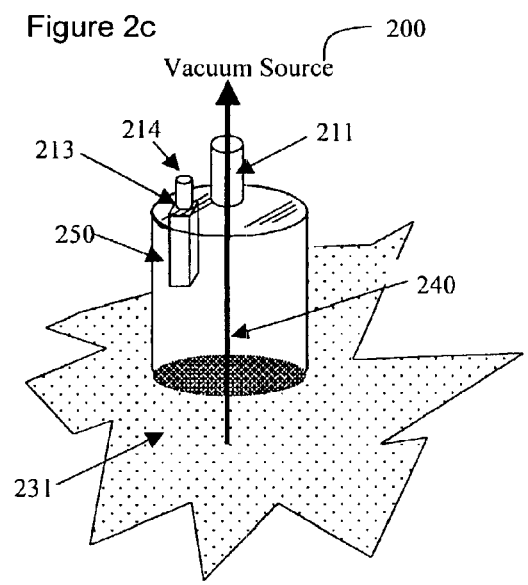
FIG. 2c shows the embodiment of FIG. 2b used to capture a desired amount of material suspended in a gas.

FIG. 2*c* shows application of the device and configuration of the present invention described in association with FIG. 2*b* where sample suspension 221 consists of particulate matter, for example, soot, suspended in a gas, for example air.

Figure 3A:
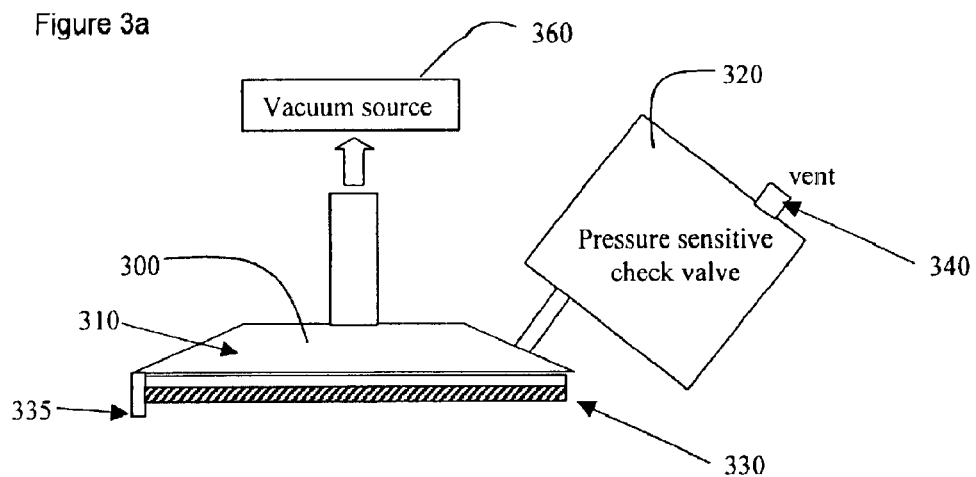
FIG. 3a shows a membrane filter apparatus with pressure-sensitive check valve.

FIG. 3*a* shows an embodiment of the present invention 300 comprised of a hollow main body 310 and a pressure-sensitive check valve 320 extending into the main body 310 so as to communicate with one side of a membrane filter 330, which is attached to the underside of the main body 310. As desired, for use in fluids, a protrusion 335 may be provided on the bottom of the main body 310 or may be fashioned appropriately to stop the membrane filter 330 from contacting the bottom of a sample vessel (not shown) and disrupting flow during use. A vacuum source 360 is provided for sample aspiration. Initially, the vent portion 340 of the pressure-sensitive check valve 320 is closed and typically, the membrane filter 330 is fresh (free of sample material). To begin collection, vacuum is used to draw sample suspension (not shown) through the membrane filter 330 causing material to collect on the underside of the membrane filter 330. Accordingly, as material collects, the pores becomes occluded and the rate of flow of sample suspension decreases. The pressure-sensitive check valve 320 monitors flow rate through the membrane filter 320 and when the flow rate falls to a desired level, thus indicating that a desired amount of material has been collected, the pressure-sensitive check valve 320 triggers (at a predetermined pressure) and sample flow (and material collection) is halted. Descriptions of filter collection systems that utilize electronics to accomplish a comparable task may be found in U.S. Pat. No. 6,010,909 and U.S. Pat. No. 6,225,125. A portion of this prior art is presented in FIGS. 1 and 2 herein. Although various filters may be employed in such a configuration, for preparing cytological samples, the membrane filter 330 typically has relatively uniformly-distributed pores of a uniform size, intended to capture material larger than the pore size, while passing particulate material that is small. Approximately half a dozen companies provide a filter apparatus that is adapted to a syringe (syringe filters).

For one embodiment of the present invention, the sensor portion of the pressure-sensitive check valve 320 has been adjusted to trigger at a desired, predetermined pressure which is established to indicate capture of a desired quantity of material on the bottom surface of the membrane filter 330. As diagrammed, when the pressure-sensitive check valve 320 triggers (indicating that a desired amount of material has been captured), a pathway is opened which vents off the vacuum, thereby stopping the aspiration of sample. While it is one object of the present invention to minimize or eliminate electronics that communicate with the pressure transducer or control systems, a battery-powered pressure transducer and/or valve assembly is consistent with this objective. As desired, the pressure-sensitive check valve 320 could be implemented in a variety of other ways so as to monitor and control sample flow, for example upon triggering it could close a fluid pathway. For biological applications, or when other dangers are present, it may be preferable to vent the vacuum as described which serves to limit the potential for aerosols.

To simultaneously prepare several samples, vacuum could be provided by a stepper-driven syringe, with one syringe for each sample. For higher levels of automation a vacuum pump and vacuum isolators may be preferred. Accordingly, material capture by the present invention may be transferred by contacting an appropriate receiving surface. For some applications, such as machine vision examination of cytological samples, monolayer deposition may be made to the underside of a cover-glass or other relatively thin, uniform material, such as transparent tape, thereby providing material at approximately the same distance from the top surface to facilitate focus. To provide additional rigidity, the thin receiving surface may be placed or affixed to a second surface as desired, or required.

Figure 3B:
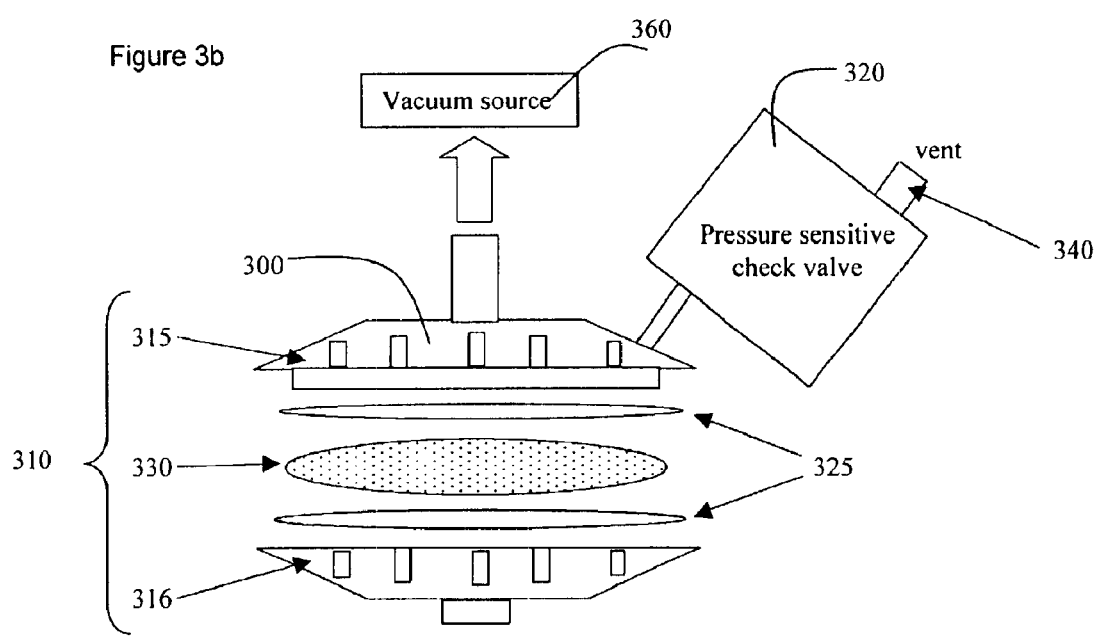
FIG. 3b shows another configuration of membrane filter apparatus.

FIG. 3*b* shows an alternative configuration of present filter device 300, this time having upper body portion 315 and lower body portion 316. A membrane filter 330 is shown to be sealed with the formed body by O-rings 325. The upper and lower body portions 315 and 316 are designed so as to join and seal with the O-rings 325, establishing conditions for sample flow to be substantially through the membrane filter 330. For some applications, once a desired quantity of material is captured on the filter, it may be useful to re-suspend this material by back-flushing the filter. Once material is re-suspended, for example, another filter device may be used to isolate a sub-component of the material collected. Alternatively, if access to the filter surface is desired, the upper body 315 and the lower body 316 should be made separable using a press-fit, threads or other convenient form of assembly.

A pressure-sensitive check valve 320 is shown in communication with the upper body portion 315 of the filter 335. Again, flow through the membrane filter 330 decreases with time due to progressive obstruction of the pores by material as it collects. The pressure-sensitive check valve 320 senses flow rate therefore, providing a measure of the amount of material captured by the membrane filter 330.

Figure 3C:
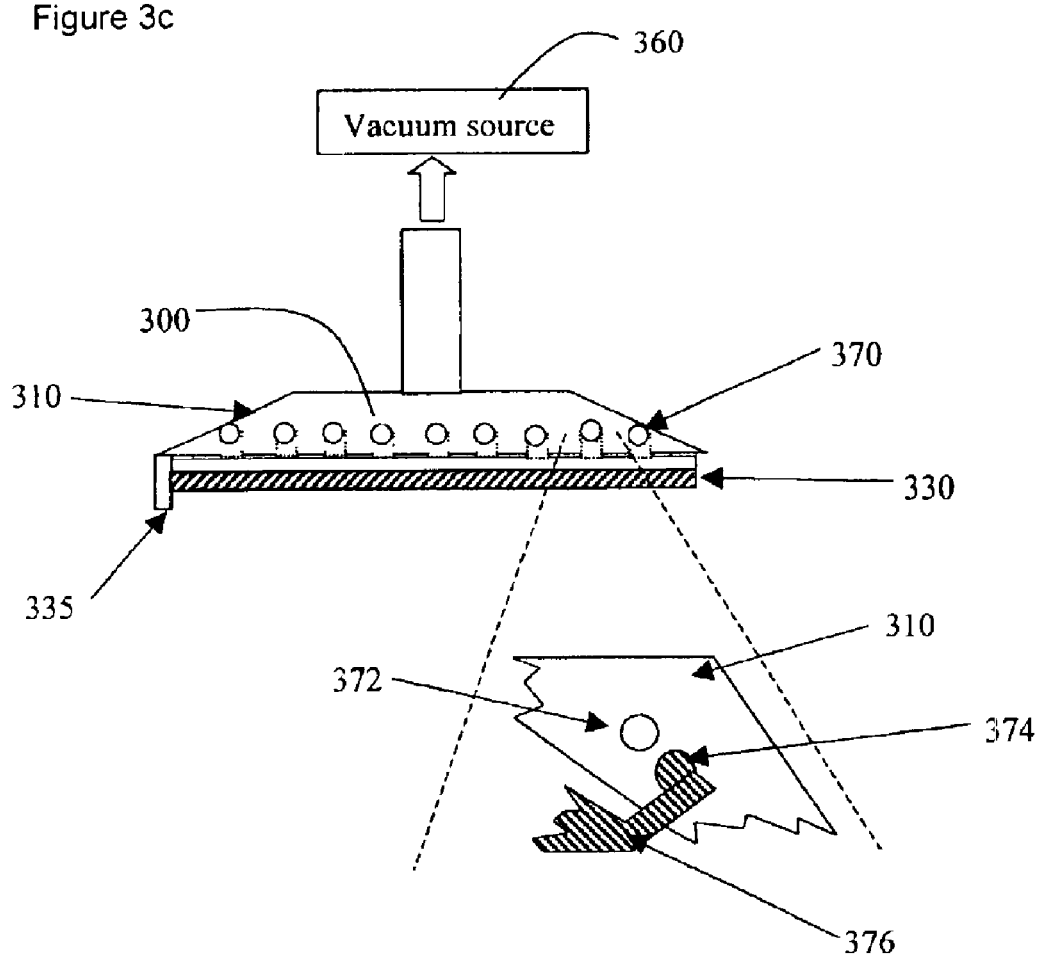
FIG. 3c shows an embodiment of the present invention, incorporating a pressure-sensitive check valve in the form of spring tabs arranged around the periphery of a filter apparatus.

FIG. 3c shows an embodiment of the present invention having a membrane filter 330 (not shown) attached on the lower surface of the device body 310. As described in association with FIG. 3a, a standoff 335 may be provided. In this embodiment the pressure-sensitive check valve 370 is integrated and implemented around the periphery of the apparatus with plastic spring tabs that operate as poppet valves. These are further diagrammed in expanded view. Plastic spring tab 376 has contact area 374, tension sealed into vent hole 372 in the wall of the device body 310. Although a single poppet valve of this type could function as a pressure-sensitive check valve for the intended use, such functionality has been implemented using a plurality of plastic poppet valves 370 distributed around the periphery of filter device 300. As described in association with FIGS. 3a and 3b, applied vacuum 360 initiates the flow of sample suspension (not shown) through the membrane filter 330. And as material is captured on the underside of membrane filter 330, the pressure-sensitive poppet valves 370 are in communication with the upper side of the membrane filter 330, so positioned so as to monitor the flow rate of material through the membrane filter 330. The poppet valve(s) are set to trigger at a predetermined pressure to indicate when a desired quantity of material has been collected on the membrane filter 330.

As discussed, the pressure-sensitive check valve 370 may be implemented with one or more contact tabs. Compound valves of this type may be adjusted to trigger or otherwise activate at a predetermined pressure. Similarly, the characteristics of the valve portion may also be made adjustable, for example, when used as a vent or fluid pathway the diameter of the valve could be adjusted. For some applications or reasons of manufacture, size, operating range, reliability, sensitivity, trigger rate, etc. it may be desirable to distribute a plurality of these plastic spring tabs around the periphery of the device, as shown. Such tab(s) may be affixed as separate units, be fabricated as a ring of units designed for insertion into the device body or it may be preferable to establish these pressure-sensitive check valve components as part of a molding process. Again, the application, costs and other factors may influence implementation.

Figure 4:
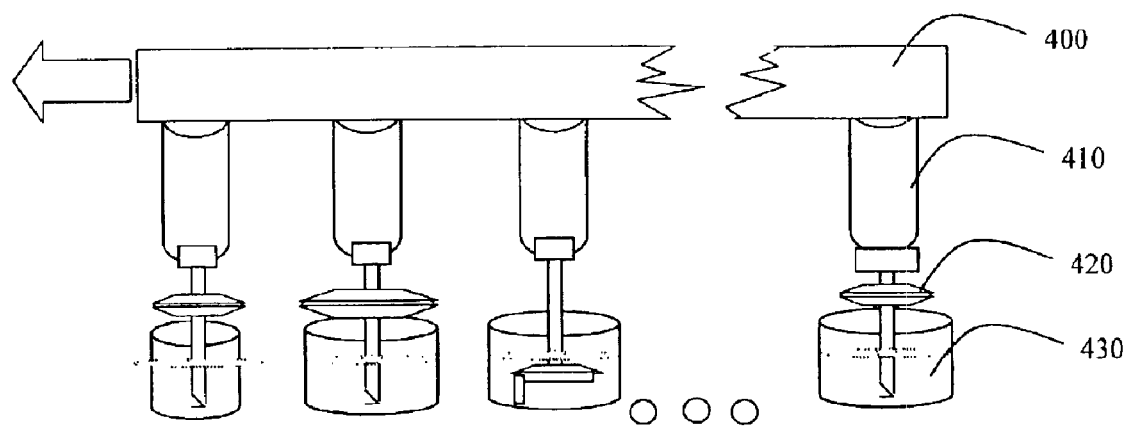
FIG. 4 shows an embodiment of the present invention utilized to process a plurality of samples.

FIG. 4 shows a configuration of filter devices of the present invention for processing a plurality of samples. A vacuum manifold 400 distributes vacuum which is further isolated via vacuum chambers 410. Material in suspension 430 begins to be aspirated into filter device(s) 420. Accordingly, by selecting appropriate components, a plurality of similar or different samples may be processed simultaneously. Alternatively, each station may be established to capture the same amount of material, or different amounts of material as desired, or required.

Figure 5A:
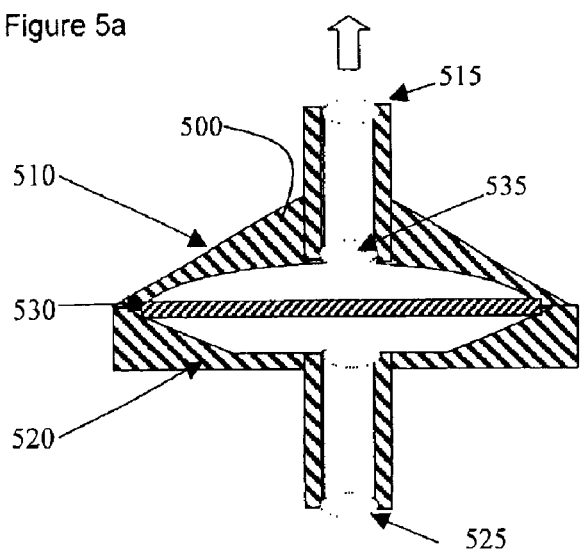
FIG. 5a shows a syringe filter assembly of an embodiment of the present invention where a deformable filter provides flow rate monitoring (pressure detection) and flow rate control.

FIG. 5a shows a filter device 500 of the present invention with a membrane filter 530 interposed between upper body 510 and lower body 520. Sample suspension (not shown) enters through inlet port 525, passes through the membrane filter 530 and exits via outlet port 515. In this instance, the membrane filter 530 is selected with sufficient deformability so as to generally conform to the interior surface 535 of the upper device body 510 when a desired amount of material (indicated by the reduced flow rate through the membrane filter 530) has been captured. Accordingly, flow is subsequently restricted to a smaller area of the membrane filter 530, for example a single central fluid pathway, as diagrammed.

Figure 5B:
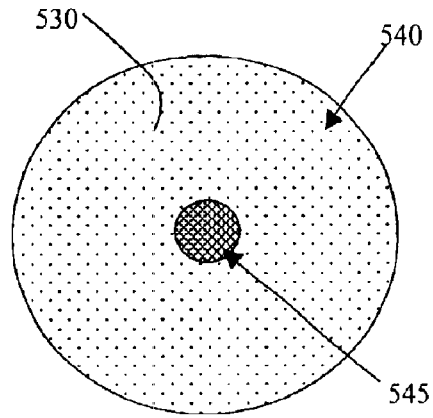

FIG. 5b shows such a filter 530, as described in association with FIG. 5a, having captured a desired amount of material in region 540 and providing reduced flow through a more restricted area of the filter 545. As desired, sample flow may continue or be allowed to continue, for example, until area 545 occludes so as to slow or substantially reduce or stop sample flow, as such continuation has no subsequent effect as the desired amount of material has been captured in area 540 of the filter. The device may continue to draw sample as desired without substantially affecting the desired amount of material collected in region 540. As desired the upper body 315 and lower body 316 may be made separable to provide filter access.

Figure 6A:
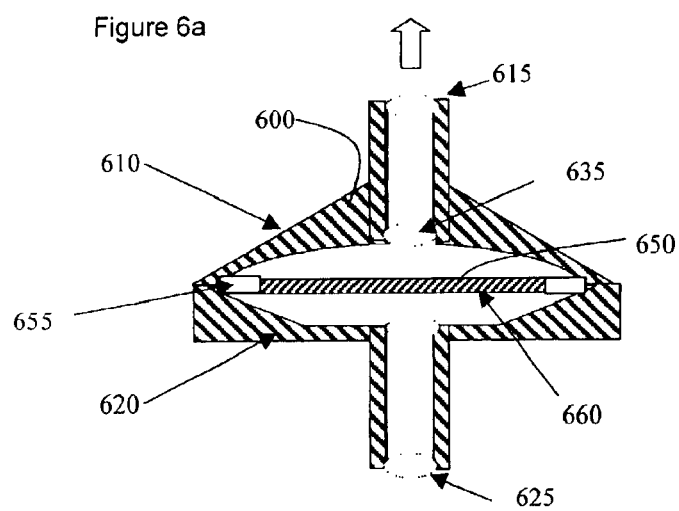
FIG. 6a show yet another embodiment of a filter assembly to monitor and control or otherwise adjust flow rate through a filter.

FIG. 6a shows a filter device 600 of the present invention with a membrane filter assembly 650 interposed between upper body 610 and lower body 620. Sample suspension (not shown) enters through inlet port 625, passes through the membrane filter assembly 650 and exits via outlet port 615. The membrane filter assembly 650 is comprised of a filter 660 and surrounding non-porous support structure 655. In this instance, the membrane filter assembly 650 acts as a pressure transducer, responding to a reduction in flow rate through the filter 660 as particulate material collects on the underside of the filter 660. As described in association with FIGS. 5a and 5b, deformation of the filter, or in this instance the membrane filter assembly 650, provides the means to alter flow in response to the pressure differential across the membrane filter assembly 650.

Figure 6B:
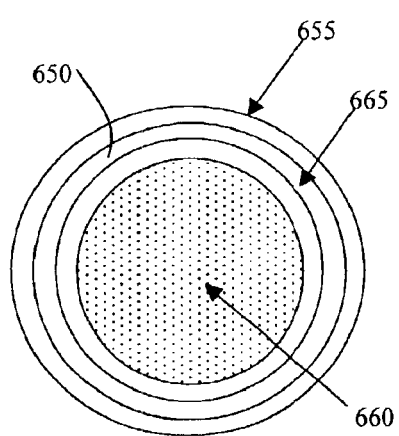

FIG. 6b shows the membrane filter assembly 650 having a filter area 660 supported by a surrounding non-porous support structure 655. The support structure 655 has striations 665 allowing it to deform in a triggered motion when a predetermined pressure is sensed. As described, material collecting on the underside of the filter 660 begins to occlude the filter 660, contributing to a reduction in flow rate through the filter 660 and a pressure change across the membrane filter assembly 650. When a desired amount of material has been collected the support structure triggers so as to conform to the inner surface as described in association with FIG. 5a or the support structure may contact a valve as described in association with FIGS. 3a, b and c so as to substantially stop sample flow and therefore halt material collection.

Figure 6C:
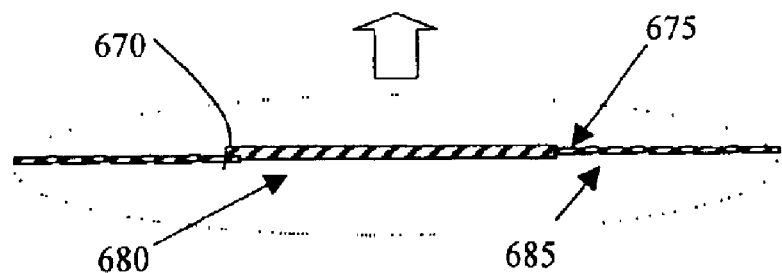
FIG. 6c shows an embodiment of a filter assembly at rest (under normal operating conditions).

FIG. 6c shows a membrane filter assembly 670 having a filter area 680 in surrounding nonporous support structure 675. The support structure 675 has striations 685. The membrane assembly is diagrammed in a first state which is substantially maintained until the pressure differential across the membrane filter assembly 670 reaches a predetermined trigger point at which time the structure toggles or deforms to a second state.

Figure 6D:
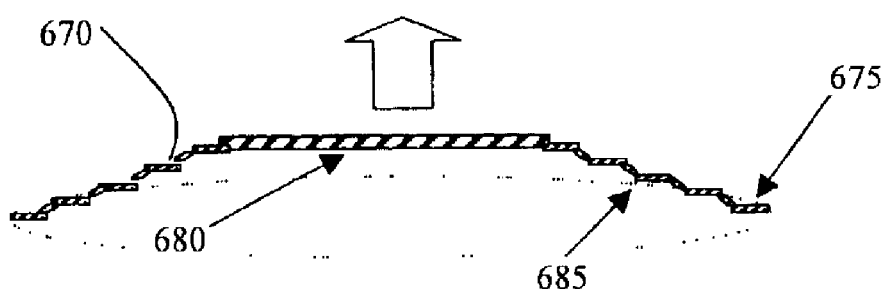
FIG. 6d shows the filter assembly embodiment of FIG. 6c in an activated state having responded to pressure changes indicative of collecting a desired amount of material.

FIG. 6d shows the membrane filter assembly 670 as discussed in association with FIG. 6c in a triggered or deformed state. As desired or required, the membrane filter assembly 670 may itself provide a means to alter flow when the state toggles, indicating collection of a desired amount of material on the filter 680. Alternatively, the state change may contact a valve, a switch or valve interfaced to a switch so that flow through the membrane may be adjusted, or halted.

While preferred embodiments of the present invention are shown and described, it is envisioned that those skilled in the art may devise various modifications of the present invention without departing from the spirit and scope of the appended claims.

I claim:

1. An apparatus for capturing a desired quantity of material from a sample suspension on a filter, comprising:

a body member defining a chamber and having opposed ends, an outlet port in one of said ends, and an inlet port;

said inlet port and said outlet port defining a single pathway for sample suspension to flow though said apparatus;

a substantially planar filter mounted within said chamber between said inlet port and said outlet port and completely across said single pathway, so that sample suspension flowing through said apparatus must flow from said inlet port through said filter and to said outlet port;

said filter being deformable toward said outlet end at a predetermined pressure change across said filter and having a first porous portion and a second porous portion concentrically arranged centrally of said first portion, said second portion constructed to be more restrictive to flow than said first portion, said predetermined pressure change selected so that when a desired quantity of material has been captured by said first portion, said substantially planar filter deforms against said outlet end such that all flow of sample suspension through said apparatus must flow through said more restrictive second portion; and means for providing a pressure to cause said sample suspension to flow through said apparatus.

* * * * *